United States Patent [19]
Zadina et al.

[11] Patent Number: 5,885,958
[45] Date of Patent: Mar. 23, 1999

[54] MU-OPIATE RECEPTOR PEPTIDES

[75] Inventors: James E. Zadina; Abba J. Kastin; Laszlo Hackler, all of Metairie, La.

[73] Assignee: Administrators of the Tulane Educational Fund, New Orleans, La.

[21] Appl. No.: 824,109

[22] Filed: Mar. 25, 1997

[51] Int. Cl.$^6$ .............................. A61K 38/12; C07K 5/12
[52] U.S. Cl. ................... 514/9; 514/11; 514/18; 435/7.1; 436/86; 436/501
[58] Field of Search ...................... 530/317, 330; 514/9, 11, 18; 435/7.1; 436/86, 501

[56] References Cited

U.S. PATENT DOCUMENTS

| | | | |
|---|---|---|---|
| 4,350,627 | 9/1982 | de Castiglione et al. | 260/112.5 |
| 5,312,899 | 5/1994 | Schiller | 530/331 |
| 5,455,230 | 10/1995 | Schiller | 514/18 |

FOREIGN PATENT DOCUMENTS

| | | |
|---|---|---|
| 9522557 | 8/1995 | WIPO . |
| WO 95/22557 | 8/1995 | WIPO . |
| WO 96/40208 | 12/1996 | WIPO . |
| WO 97/03210 | 1/1997 | WIPO . |
| WO 97/07130 | 2/1997 | WIPO . |

OTHER PUBLICATIONS

Sakaguchi et al., Bull. Chem. Soc. JPN 65 No. 4 1052–1056 (1992).

Schiller, et al., *Proc. Natl. Acad. Sci. USA*. 89:11871–11875 (1992).

Schiller, et al., *J. Med. Chem.* 32:698–703 (1989).

Dooley, et al., *Peptide Res.* 8:124–137 (1995).

Zadina, et al., *Life Sci.* 55:PL 461–466 (1994).

Zadina, et al., *Peptides.* 15:1567–1569 (1994).

Makarov et al., *Cell* 88:657–666 (1997).

Zadina et al., *Nature* 38613:499–502 (1997).

Schiller et al., *Journal of Medicinal Chemistry* 32:698–703 (1989).

Sakaguchi et al., *Bull. Chem. Soc. Jpn.* 65:1052–1056 (1992).

Schiller et al., *Advances in the Biosciences* 75:85–88 (1989).

*Primary Examiner*—Cecilia J. Tsang
*Assistant Examiner*—Bennett Celsa
*Attorney, Agent, or Firm*—Arnold, White & Durkee

[57] ABSTRACT

This invention relates to certain peptides and linear and cyclic analogs thereof that bind to the mu (morphine) opiate receptor with higher affinity, selectivity and potency than currently available peptides. This invention also relates to pharmaceutical preparations containing an effective amount of the peptides or salts thereof, and methods for providing analgesia, relief from gastrointestinal disorders such as diarrhea, and therapy for drug dependence containing a pharmaceutically effective amount of the peptides.

25 Claims, 1 Drawing Sheet

FIG. 1

MU-OPIATE RECEPTOR PEPTIDES

The United States Government owns rights to this invention pursuant to a funding grant from the Department of Veteran Affairs Competitive Merit Review Program.

BACKGROUND OF THE INVENTION

1. Field of the Invention

This invention relates to peptides that bind with high affinity and selectivity to the mu (morphine) opiate receptor; pharmaceutical preparations containing an effective amount of the peptides or salts thereof; and methods for providing analgesia, relief from gastrointestinal disorders such as diarrhea, and therapy for drug dependence containing an effective amount of the peptides.

2. Description of Related Art

Many peptides have been found that exhibit opiate-like activity by binding to opiate receptors. Three different types of opiate receptors have been found: delta (δ), kappa (κ) and mu (μ). The major putative function for opiates is their role in alleviating pain. Other areas where opiates are well-suited for use in treatment are conditions relating to gastrointestinal disorders, schizophrenia, obesity, blood pressure, convulsions, and seizures. Although the δ and κ receptors may also mediate analgesia, activation of μ receptors is the primary and most effective means of inducing analgesia, and is the primary mechanism by which morphine acts.

To date, opiates, opioid peptides, and analogs thereof, have demonstrated a limited degree of specificity and selectivity for the receptor or receptors to which they may bind. The less selective and specific an opiate may be, the greater the chance that increased side effects from the administration of the material will be observed. When an opiate activates more than one receptor, the biological response profile for each receptor is affected, thereby potentiating a spectrum of side effects which may or may not be adverse. Such adverse side effects include heaviness of the limbs, flush or pale complexion, clogged nasal and sinus passages, dizziness, and depression. Compounds that activate κ receptors frequently induce dysphoria.

Peptides have been identified in mammalian brain that are considered endogenous agonists for δ (enkephalins) and κ (dynorphins) opiate receptors, but none show clear preference for the μ receptor. Tyr-W-MIF-1 (Tyr-Pro-Trp-Gly-NH$_2$) (SEQ ID NO:27) is an endogenous peptide isolated from human (1) and bovine (2) brain with opiate-related activity in the guinea pig ileum (1,2,3) and in tests of analgesia (4,5,6). It is highly selective for μ over δ and κ receptors (>200- and 300-fold), but its μ receptor affinity (Ki=70 nM) is relatively low (7). Numerous analogs have been made, most of which are based on modifications of the naturally occurring enkephalins that prefer the δ opiate receptor, or dynorphins that prefer the K receptor. In addition, most of these analogs are relatively hydrophilic, limiting their access to the central nervous system.

Because morphine and other compounds with clinical usefulness act primarily at the μ receptor, endogenous peptides with high affinity and selectivity for this site would be of considerable importance. These peptides, and analogs based on such peptides, that have a natural selectivity for the μ receptor would be advantageous for activating the μ receptor. It would also be desirable to synthesize these peptides in a simple, efficient, and economical manner to facilitate the preparation of suitable quantities for toxicological studies and commercial suppliers while retaining the optical integrity of the desired materials.

SUMMARY OF THE INVENTION

This invention relates to certain peptides and linear and cyclic analogs thereof that bind to the mu (morphine) opiate receptor with high affinity, selectivity and potency. These peptides have the general formula Tyr-X$_1$-X$_2$-X$_3$ wherein X$_1$ is Pro, D-Lys or D-Orn; X$_2$ is Trp, Phe or N-alkyl-Phe wherein alkyl contains 1 to about 6 carbon atoms; and X$_3$ is Phe, Phe-NH$_2$, D-Phe, D-Phe-NH$_2$ or p-Y-Phe wherein Y is NO$_2$, F, Cl or Br. This invention also relates to pharmaceutical preparations containing an effective amount of the peptides or salts thereof, and methods for providing analgesia, relief from gastrointestinal disorders such as diarrhea, and therapy for drug dependence containing an effective amount of the peptides. In preferred embodiments, the peptides of the invention have the formulas represented by:

H-Tyr-Pro-Trp-Phe-NH$_2$ (SEQ ID NO:1)
H-Tyr-Pro-Phe-Phe-NH$_2$ (SEQ ID NO:2)
H-Tyr-Pro-Trp-Phe-OH (SEQ ID NO:3)
H-Tyr-Pro-Phe-Phe-OH (SEQ ID NO:4)
H-Tyr-Pro-Trp-D-Phe-NH$_2$ (SEQ ID NO:5)
H-Tyr-Pro-Phe-D-Phe-NH$_2$ (SEQ ID NO:6)
H-Tyr-Pro-Trp-pNO$_2$-Phe-NH$_2$ (SEQ ID NO:7)
H-Tyr-Pro-Phe-pNO$_2$-Phe-NH$_2$ (SEQ ID NO:8)
H-Tyr-Pro-N-Me-Phe-Phe-NH$_2$ (SEQ ID NO:9)
H-Tyr-Pro-N-Et-Phe-Phe-NH$_2$ (SEQ ID NO: 10)
H-Tyr-Pro-N-Me-Phe-D-Phe-NH$_2$ (SEQ ID NO:I 1)
H-Tyr-Pro-N-Et-Phe-D-Phe-NH$_2$ (SEQ ID NO: 12)
H-Tyr-c-[D-Lys-Trp-Phe]
H-Tyr-c-[D-Lys-Phe-Phe]
H-Tyr-c-[D-Orn-Trp-Phe]
H-Tyr-c-[D-Orn-Phe-Phe]
H-Tyr-c-[D-Lys-Trp-pNO$_2$-Phe]
H-Tyr-c-[D-Lys-Phe-pNO$_2$-Phe]
H-Tyr-c-[D-Om-Trp-pNO$_2$-Phe]
H-Tyr-c-[D-Orn-Phe-pNO$_2$-Phe]
H-Tyr-c-[D-Lys-N-Me-Phe-Phe]
H-Tyr-c-[D-Orn-N-Me-Phe-Phe]
H-Tyr-c-[D-Lys-N-Et-Phe-Phe]
H-Tyr-c-[D-Orn-N-Et-Phe-Phe]
H-Tyr-c-[D-Lys-N-Me-Phe-D-Phe]
H-Tyr-c-[D-Lys-N-Et-Phe-D-Phe]

The last fourteen peptides listed are cyclic peptides whose linear primary amino acid sequences are given in SEQ ID NO:13 through SEQ ID NO:26.

BRIEF DESCRIPTION OF THE DRAWINGS

The following drawing forms part of the present specification and is included to further demonstrate certain aspects of the present invention. The invention may be better understood by reference to this drawing in combination with the detailed description of specific embodiments presented herein.

DESCRIPTION OF ILLUSTRATIVE EMBODIMENTS

This invention relates to peptides that bind to the mu (morphine) opiate receptor; pharmaceutical preparations containing an effective amount of the peptides or salts thereof; and methods for providing analgesia, relief from gastrointestinal disorders such as diarrhea, and therapy for drug dependence containing an effective amount of the peptides. The peptides of the invention have the general formula Tyr-$X_1$-$X_2$-$X_3$ wherein $X_1$ is Pro, D-Lys or D-Orn; $X_2$ is Trp, Phe or N-alkyl-Phe wherein alkyl contains 1 to about 6 carbon atoms; and $X_3$ is Phe, Phe-$NH_2$, D-Phe, D-Phe-$NH_2$ or p-Y-Phe wherein Y is $NO_2$, F, Cl or Br. Some preferred embodiments of the invention are peptides having the formulas represented by:

H-Tyr-Pro-Trp-Phe-$NH_2$ (SEQ ID NO: 1)
H-Tyr-Pro-Phe-Phe-$NH_2$ (SEQ ID NO:2)
H-Tyr-Pro-Trp-Phe-OH (SEQ ID NO:3)
H-Tyr-Pro-Phe-Phe-OH (SEQ ID NO:4)
H-Tyr-Pro-Trp-D-Phe-$NH_2$ (SEQ ID NO:5)
H-Tyr-Pro-Phe-D-Phe-$NH_2$ (SEQ ID NO:6)
H-Tyr-Pro-Trp-p$NO_2$-Phe-$NH_2$ (SEQ ID NO:7)
H-Tyr-Pro-Phe-p$NO_2$-Phe-$NH_2$ (SEQ ID NO:8)
H-Tyr-Pro-N-Me-Phe-Phe-$NH_2$ (SEQ ID NO:9)
H-Tyr-Pro-N-Et-Phe-Phe-$NH_2$ (SEQ ID NO: 10)
H-Tyr-Pro-N-Me-Phe-n-Phe-$NH_2$ (SEQ ID NO: 11)
H-Tyr-Pro-N-Et-Phe-D-Phe-$NH_2$ (SEQ ID NO: 12)
H-Tyr-c-[D-Lys-Trp-Phe]
H-Tyr-c-[D-Lys-Phe-Phe]
H-Tyr-c-[D-Orn-Trp-Phe]
H-Tyr-c-[D-Orn-Phe-Phe]
H-Tyr-c-[D-Lys-Trp-p$NO_2$-Phe]
H-Tyr-c-[D-Lys-Phe-p$NO_2$-Phe]
H-Tyr-c-[D-Orn-Trp-p$NO_2$-Phe]
H-Tyr-c-[D-Orn-Phe-p$NO_2$-Phe]
H-Tyr-c-[D-Lys-N-Me-Phe-Phe]
H-Tyr-c-[D-Orn-N-Me-Phe-Phe]
H-Tyr-c-[D-Lys-N-Et-Phe-Phe]
H-Tyr-c-[D-Orn-N-Et-Phe-Phe]
H-Tyr-c-[D-Lys-N-Me-Phe-D-Phe]
H-Tyr-c-[D-Lys-N-Et-Phe-D-Phe]

The last fourteen peptides listed are cyclic peptides whose linear primary amino acid sequences are given in SEQ ID NO: 13 through SEQ ID NO:26.

The peptide of SEQ ID NO:1 is highly selective and very potent for the $\mu$ opiate receptor, with over 4000-fold weaker binding to delta receptors and over 15,000-fold weaker binding to kappa receptors, reducing the chances of side-effects. Following identification of the synthesized peptide, the peptide was isolated from brain. The peptide of SEQ ID NO:2 was then synthesized and shows a $\mu$ receptor affinity about half that of the peptide of SEQ ID NO:1, but a selectivity that is about 3-fold higher. This peptide was also isolated from the brain.

Both peptides of SEQ ID NO:1 and SEQ ID NO:2 differ structurally from previously known endogenous opioids in their N-terminal (Tyr-Pro) sequence, C-terminal amidation, and tetrapeptide length. In addition, the peptide of SEQ ID NO:1 is the first high affinity ligand to contain Trp rather than Phe as the second aromatic moiety. Although other peptides with this feature have been reported (8–10), their affinity is low, and the best known (hemorphin) is derived from enzymatic digests (8). β-casomorphins (11) contain the Tyr-Pro-Phe sequence found in the peptide of SEQ ID NO:2, but contain the less active Pro in position 4, and are not known to be present in neuronal tissue.

Both linear and cyclic analogs of the peptides of SEQ ID NO:1 and SEQ ID NO:2 were subsequently made. The linear analogs are given in SEQ ID NO:3 through SEQ ID NO:12. The cyclic peptides have linear primary amino acid sequences given in SEQ ID NO:13 through SEQ ID NO:26, wherein the cyclization joins amino acids 2 and 4 in the sequence. Analogs of enkephalin and β-casomorphin have resulted in compounds with either more selective binding than the parent compound or greater activity due to increased affinity or decreased susceptibility to enzymatic degradation. Thus, the linear and cyclic analogs of this invention were synthesized to further improve binding, bioactivity and stability of the natural peptides.

Similarly, modification of the second aromatic moiety (Phe) in enkephalin (12) and casomorphin (13) peptides by N-alkylation has increased the $\mu$ receptor selectivity and stability over parent compounds. Analogs of SEQ ID NO:2 may be made wherein the phenylalanine in position 3 is in the N-alkylated form. Alkyl groups suitable in the peptides of the present invention contain 1 to about 6 carbon atoms, and the alkyl group is preferably methyl or ethyl. Linear analogs having SEQ ID NO:9 through SEQ ID NO:12 and cyclic analogs whose linear primary amino acids sequences are given in SEQ ID NO:21 through SEQ ID NO:26 have N-methylated or N-ethylated phenylalanine in position 3. Analogs may also be made wherein the amino acid at position 4 is p-Y-phenylalanine, wherein Y is $NO_2$, F, Cl or Br, in order to enhance $\mu$ receptor binding and potency (14). Linear analogs having SEQ ID NO:7 and SEQ ID NO:8, and cyclic analogs whose linear primary amino acids sequences are given in SEQ ID NO:17 through SEQ ID NO:20 have p-nitrophenylalanine (p$NO_2$-Phe) in position 4.

The peptides of this invention may be prepared by conventional solution-phase (15) or solid phase (16) methods with the use of proper protecting groups and coupling agents. A suitable deprotection method may then be employed to remove specified or all of the protecting groups, including splitting off the resin if solid phase synthesis is applied.

A variety of protecting groups known in the field of peptide synthesis and recognized by conventional abbreviations therein, may be found in T. Greene, *Protective Groups In Organic Synthesis*, Academic Press (1981). Some preferred protecting groups that may be utilized include, $N^\alpha$-Boc ($N^\alpha$-tert-butyloxycarbonyl), $N^W$-Z ($N^W$-benzyloxycarbonyl), and -Obzl (-O-benzyl).

Carbodiimide, active ester, and mixed anhydride methods may be used in the coupling reactions. A preferred technique uses the dicyclohexylcarbodiimide (DCC) method that can be used with or without catalytic additives such as 1-hydroxybenztriazole (HOBt) to hasten the reaction and suppress the racemization of the desired compound.

The DCC and active OSu (N-hydroxysuccinimide) ester coupling reactions can be performed mostly at room temperature but may be carried out from about $-78\,°$ C. to room temperature. The solvents are polar and aprotic organic solvents. Preferred solvents include dichloromethane (DCM), chloroform, and N,N'-dimethylformamide (DMF). In general, the time required for the coupling may be between 3 and 48 hours. Preferably, the reaction is carried out at about $-10°$ C. to $25°$ C. with stirring or shaking for about 4–12 hours.

The solid phase synthesis of linear peptides can be performed on Merrifield resins (free peptide acids), and benzhydrylamine or 4-methyl-benzhydrylamine resin with the DCC/HOBt method.

Cyclization of the linear peptides can be performed upon substitution of an appropriate diamino carboxylic acid for Pro in position 2 in the peptides through ring closure of the 2-position side chain amino and the C-terminal carboxylic functional groups. The cyclization reactions can be performed with the diphenylphosphoryl azide method (17).

The deprotection of Boc peptides can be performed with 100% trifluoroacetic acid (TFA) in the solution syntheses, and with 25% TFA/DCM in the solid phase syntheses in the presence of the antioxidant dithiothreitol, and m-cresol or anisole as scavenger. The OBzl and Z protecting groups may be removed with hydrogenolysis on 10% palladium/charcoal (Pd/C) in 80% acetic acid.

Peptides synthesized with solid phase synthesis can be split off the resin with liquid hydrogen fluoride (HF) in the presence of the proper antioxidant and scavenger.

The amounts of the reactants utilized in the reactions, as well as the conditions required to facilitate the reactions and encourage efficient completion may vary widely depending on variations in reaction conditions and the nature of the reactants.

The desired products may be isolated from the reaction mixture by crystallization, electrophoresis, extraction, chromatography, or other means. However, a preferred method of isolation is HPLC. All of the crude peptides can be purified with preparative HPLC, and the purity of the peptides may be checked with analytical HPLC. Purities greater than 95% of the synthesized compounds using HPLC have been obtained.

The present invention also provides pharmaceutical preparations which contain a pharmaceutically effective amount of the peptides, or salts thereof, of this invention and a pharmaceutically acceptable carrier or adjuvant. The carrier may be an organic or inorganic carrier that is suitable for external, enteral or parenteral applications. The peptides of the present invention may be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems (18), and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form, and in addition auxiliary, stabilizing, thickening and coloring agents and perfumes may be used.

The present invention also provides methods for providing analgesia, relief from gastrointestinal disorders such as diarrhea, and therapy for drug dependence in patients, such as mammals, including humans, which comprises administering to the patient an effective amount of the peptides, or salts thereof, of this invention. The diarrhea may be caused by a number of sources, such as infectious disease, cholera, or an effect or side-effect of various drugs or therapies, including those used for cancer therapy. For applying the peptides of the present invention to human, it is preferable to apply it by parenteral or enteral administration. The dosage of effective amount of the peptides varies from and also depends upon the age and condition of each individual patient to be treated. However, suitable unit dosages may be between about 0.01 to about 100 mg. For example, a unit dose may be from between about 0.2 mg to about 50 mg. Such a unit dose may be administered more than once a day, e.g. two or three times a day.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Peptides containing all possible natural amino acid substitutions in position 4 of Tyr-W-MIF-1 (H-Tyr-Pro-Trp-Gly-NH$_2$) (SEQ ID NO:27) were synthesized by polyethylene pin technology (19). The relative affinity and selectivity for the $\mu$ receptor over the $\delta$ and $\kappa$ receptors of the synthesized peptides were tested and compared. Binding of the peptides to opiate receptors was measured by inhibition of [$^3$H]-DAMGO (60 Ci/mmol) for $\mu$ receptors, $^3$H-pCl-DPDPE (49 Ci/mmol) for $\delta$ receptors, or $^3$H-ethylketocyclazocine (EKC) (18 Ci/mmol) in the presence of 100 nM DAMGO and DPDPE (to quench $\mu$ and $\delta$ binding) for $\kappa$ receptors (7).

Figure 1:
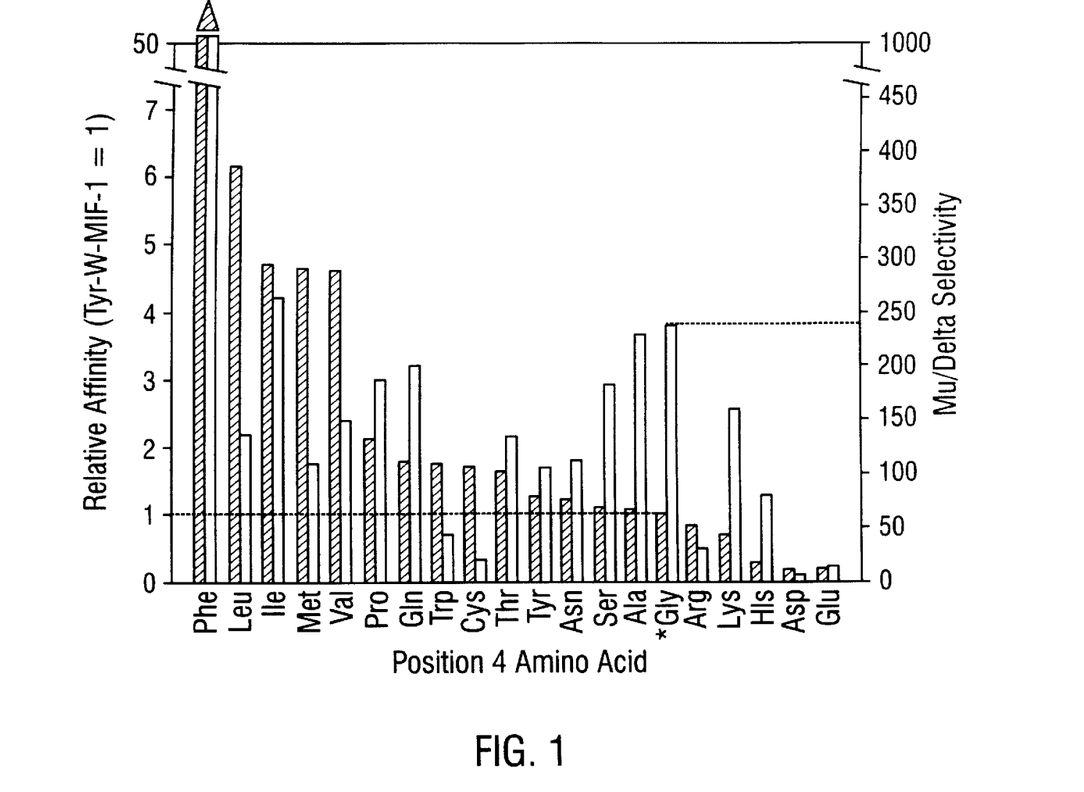
FIG. 1 shows the unexpectedly high affinity and selectivity for the mu opiate receptor of SEQ ID NO:1 relative to 19 peptide analogs with which it was compared. The Ki for the μ opiate receptor is shown on the left Y-axis, expressed relative to that of Tyr-W-MIF-1 (Tyr-Pro-Trp-Gly-NH$_2$) (SEQ ID NO:27) (85 nM) in the solid black bars. The dashed line from the left axis to the bar for Tyr-W-MIF-1 (position 4=Gly (*)) illustrates the affinity ratio of 1. The selectivity for μ over δ receptors (δ Ki /μ Ki) is shown on the right Y-axis and with open bars. The dashed line from the right axis to the bar for Tyr-W-MIF-1 (*Gly) represents the 240-fold selectivity of Tyr-W-MIF-1 for μ receptors. The arrow above the Phe analog indicates that its extraordinary affinity and selectivity were well above the range of the other compounds. Values represent the mean of 2 separate assays with each of 2 separate syntheses of the set of 20 peptides.

FIG. 1 shows the relative affinity of each peptide for the $\mu$ receptor (solid bars). The peptide with Phe in the fourth position had increased affinity that considerably exceeded the scale useful for illustrating the differences among the other peptides. Its affinity estimated from two peptide sets was over 50-fold greater than that of the parent compound, Tyr-W-MIF-1, with Gly in position 4.

The selectivity of the peptides for $\mu$ over $\delta$ receptors is also shown in FIG. 1 (open bars) relative to that of Tyr-W-MIF-1, which had a selectivity ratio of 240-fold in these assays. The parent peptide, Tyr-W-MIF-1, proved to be one of the most selective in the set. As with the affinity at the $\mu$ receptor, however, the selectivity ratio for $\mu$ sites of the peptide with Phe in the fourth position was well above the scale for the remainder of the peptides.

A more hydrophobic amino acid after the second aromatic residue tended to increase $\mu$ receptor binding. The correlation between binding (IC$_{50}$) and the hydrophobicity of uncharged amino acids in position 4 was significant (p<0.001). Based on the r$^2$ value (0.56), however, only about half of the variance in binding affinity was attributable to hydrophobicity, and the binding of the peptide of SEQ ID NO:1 was >2 standard error units stronger than predicted from the regression. This indicates that physicochemical factors in addition to hydrophobicity are important for its high binding affinity.

The affinity and selectivity of the peptide of SEQ ID NO: 1 is also compared to currently available peptides. Table I shows that, in comparison to one of the most potent and $\mu$-selective analogs of enkephalin available (DAMGO), the peptide of SEQ ID NO:1 has an equal affinity and greater selectivity for the $\mu$ receptor. Table I also shows that this peptide is more potent and selective than the peptides generally considered endogenous ligands for the $\mu$ receptor (β-endorphin and Met-enkephalin). This peptide is also more potent than dynorphin, which binds preferentially to the $\kappa$ receptor and is considered the endogenous ligand for that site but also has high affinity for the $\mu$ receptor. Thus, the peptide of SEQ ID NO:1 has higher affinity and selectivity for the $\mu$ receptor than the three major endogenous mammalian peptides with opiate activity.

TABLE 1

Binding affinity and selectivity of various peptides.

| Peptide | Receptor Binding Ki (nM) | | | Binding Selectivity | |
|---|---|---|---|---|---|
| | $\mu$ | $\delta$ | $\kappa$ | $\delta/\mu$ | $\kappa/\mu$ |
| DAMGO | 0.34 ± 0.07 | 190 ± 16 | 1300[a] | 559 | 3824 |
| SEQ ID NO:1 | 0.36 ± 0.08 | 1506 ± 174 | 5428 ± 474 | 4183 | 15077 |
| SEQ ID NO:2 | 0.69 ± 0.16 | 9233 ± 201 | 5240 ± 460 | 13381 | 7594 |
| β-Endorphin | 4.4 ± 0.41 | | | | |
| | 2.1[b] | 2.4[b] | 96[b] | 1.1 | 46 |
| Met-Enkephalin | 5.9 ± 0.9 | | | | |
| | 9.5[b] | 0.91[b] | 4442[b] | 0.01 | 468 |
| Dynorphin | 2.0 ± 0.5 | | | | |
| | 0.73[b] | 2.4[b] | 0.12[b] | 3.3 | 0.16 |
| Tyr-W-MIF-1[a] | 70.9 | 15520 | 22300 | 219 | 314 |

[a]Values obtained from (7).
[b]Values obtained from (20).

EXAMPLE 2

The bioactivity of the peptide of SEQ ID NO:1 was tested in vitro using the guinea pig ileum assay (21). The peptide showed potent $\mu$ activity in vitro, inhibiting electrically-induced contractions of the guinea pig ileum with an $IC_{50}$ significantly more potent than that of DAMGO (3.6±0.3 nM vs. 6.8±0.8 nM, mean±SEM of four assays, $F_{1,6}$=13.4, p<0.05). The effect of the peptide was blocked and reversed by the antagonists naloxone (0.5 $\mu$M) and the $\mu$-selective CTOP (0.5 $\mu$M), but not by the κ-selective nor-binaltorphimine (20 nM), when these antagonists were applied 1 min before or after the peptide. These results confirm the $\mu$-selective bioactivity of the peptide of SEQ ID NO:1.

EXAMPLE 3

The in vivo bioactivity of the peptide of SEQ ID NO:1 was examined in tests of analgesia after intracerebroventricular (icv) (22) and intrathecal (it) (23) injection to mice. After icv injection, the peptide, with an $ED_{50}$ of 4.7 nmol [(95% CI=3.1–6.7)=2.9 $\mu$g (1.9–4.1 mg)] was at least as potent as morphine in producing analgesia [7.5 nmol (95% CI=4.8–10.5)=2.5 $\mu$g (1.6–3.5)]. Prolonged analgesia was also found to be induced by the peptide. About half the animals were still analgesic 1 hr after 10–20 $\mu$g of the peptide. By contrast, the $ED_{50}$ for the endogenous pentapeptide Met-enkephalin is 75 $\mu$g, and its effects last less than 10 min (24). The analgesia induced by 10 $\mu$g of the peptide was reversed by a low dose of naloxone (1 mg/kg, sc) and by pretreatment for 24 h with the irreversible $\mu$-selective antagonist β-funaltrexamine (40 mg/kg), reflecting its mediation by $\mu$ opiate receptors. The peptide was even more potent after injection by the it than the icv route with an $ED_{50}$ of 0.8 $\mu$g±0.4 $\mu$g. Thus, for an unmodified, all-natural amino acid tetrapeptide, the peptide of SEQ ID NO:1 is a very potent $\mu$ analgesic.

EXAMPLE 4

The affinity and selectivity of the peptide of SEQ ID NO:2 for the $\mu$ receptor was tested and compared with the values obtained for the peptide of SEQ ID NO:1. The results for SEQ ID NO:2 are shown in Table 1. The peptide of SEQ ID NO:2 showed a binding profile similar to the peptide of SEQ ID NO:1, with $\mu$ receptor affinity about half that of the peptide of SEQ ID NO:1 (0.69±0.16 nM for SEQ ID NO:2 compared with 0.36±0.08 nM for SEQ ID NO:1). The affinity at the δ receptor was about 6-fold lower. Thus, the affinity for the $\mu$ receptor is lower, but the selectivity (>13000-fold) is about 3-fold higher for SEQ ID NO:2 than for SEQ ID NO:1. The affinity for ic receptors was equally low for both.

The in vitro and in vivo bioactivites of the peptide of SEQ ID NO:2 were also tested and compared with those of the peptide of SEQ ID NO:1. The bioactivity of the peptide of SEQ ID NO:2 approached that of the peptide of SEQ ID NO:1 both in vitro ($IC_{50}$ in the guinea pig ileum assay= 4±0.4 nM) and in vivo ($ED_{50}$ for analgesia after icv injection=8.4 $\mu$g (CI=5.5–11.7). Thus, both peptides have high affinity and selectivity and potent bioactivity.

EXAMPLE 5

This example illustrates isolation of the peptides of SEQ ID NO:1 and SEQ ID NO:2 from brain extracts. An antibody was generated against the peptide of SEQ ID NO:1 and used to develop a sensitive and specific radioimmunoassay (RIA) that detects 1 pg of peptide and shows no cross-reactivity for over 40 opioid and non-opioid peptides and compounds. This RIA permitted screening of HPLC fractions from bovine cortical brain extracts and isolation of the peptide by methods previously published (2,3) with minor modifications. The isolated material was subjected to six successive cycles of automated Edman degradation. The most prevalent PTH-amino acids were easily distinguishable from the background level of amino acids, and the first four successive cycles yielded 310 pmol Tyr, 154 pmol Pro, 72 pmol Trp, and 143 pmol Phe. After the fourth cycle no further PTH-amino acid was detected above background. The peptide structure was identified as Tyr-Pro-Trp-Phe and confirmed by comparison with synthetic Tyr-Pro-Trp-Phe-NH$_2$ (SEQ ID NO:1) and its free acid, Tyr-Pro-Trp-Phe-OH (SEQ ID NO:3). The elution time of the synthetic peptide amide (21.9 min) was the same as that of the isolated peptide and was clearly separated from that of the peptide acid (25.9 min).

The only other amino acid that increased in the third cycle was PTH-Phe with a value of 51 pmol, indicating the presence of the sequence Tyr-Pro-Phe-Phe-NH$_2$ (SEQ ID NO:2). This second peptide was synthesized and there was no significant difference in the retention time of the two synthetic peptides (SEQ ID NO:1=21.9 min, SEQ ID NO:2= 21.2 min). Again, the amidated peptide was clearly separated from that of the peptide acid (25.3 min). From the 1 57g of starting material, the isolated material from the Edman degradation steps was estimated at about 200 ng, which consisted of about 80–85% Tyr-Pro-Trp-Phe-NH$_2$ (SEQ ID NO:1) and 15–20% Tyr-Pro-Phe-Phe-NH$_2$ (SEQ ID NO:2). Reminiscent of the discovery of the two ligands for the δ receptor (Met- and Leu-enkephalin), the two new peptides differ by a single amino acid. The Trp and Phe in the peptides of SEQ ID NO:1 and SEQ ID NO:2 represent the only two natural amino acids that maintain binding and activity in this position of the opioid pharmacophore (25, 26), indicating the limit of similar natural sequences.

EXAMPLE 6

Cyclic analogs to the peptides of SEQ ID NO:1 were made using the diphenyl phosphoryl azide (DPPA) method. The linear primary amino acid sequences of these cyclic analogs, H-Tyr-c-[D-Lys-Trp-Phe] and H-Tyr-c-[D-Orn-Trp-Phe] are given in SEQ ID NO:13 and SEQ ID NO:15, respectively. Binding affinities, in vitro bioactivities, and in vivo bioactivities of the analogs were determined by the methods previously given in Examples 1, 2 and 3, respectively, and compared with those of the parent peptides.

The cyclic peptide whose linear primary amino acid sequence is given in SEQ ID NO:13 (H-Tyr-c-[D-Lys-Trp-Phe]) was found to bind to the μ receptor with about 15-fold higher affinity than the peptide of SEQ ID NO:1, to have about 4-fold greater potency in the guinea pig ileum assay with a subnanomolar $IC_{50}$ and about 10-fold greater analgesic potency with an $IC_{50}$ of 0.3 μg. This cyclic peptide also proved more potent than morphine in producing analgesia in mice after IV injection, with an $ED_{50}$ of 0.16 μmol/kg compared to 0.3 μmol/kg for morphine. The cyclic peptide whose linear primary amino acid sequence is given in SEQ ID NO:15 (H-Tyr-c-[D-Orn-Trp-Phe]) was found to bind to the μ receptor with about 4-fold higher affinity than the peptide of SEQ ID NO:1.

EXAMPLE 7

Partial agonists such as buprenorphine are currently being evaluated as therapeutic agents in drug dependence (27). Such compounds can have therapeutic value and less abuse potential by providing partial activation of mu-receptor mediated cellular processes and by antagonism of the opiate effects of more efficacious compounds such as morphine. The peptides of SEQ ID NO:3 and SEQ ID NO:4 were tested for partial agonist/antagonist effects by the method of reduction of receptor reserve in the guinea pig ileum. In this procedure, partial agonists can show full agonist activity in the untreated tissue but antagonist activity when the receptor reserve is reduced by development of tolerance to morphine or by receptor alkylating agents (21). Tyr-Pro-Trp-Phe-OH (SEQ ID NO:3) and Tyr-Pro-Phe-Phe-OH (SEQ ID NO:4) showed agonist activity ($IC_{50}$=5 μM and 20 μM, respectively) in the untreated ileum. After treatment with 20 nM beta-chlornaltrexamine (B-CNA), however, these peptides showed antagonist activity. A dose of 0.3 μM DAMGO inhibited the electrically-induced contractions by 40%. Pretreatment with Tyr-Pro-Trp-Phe-OH (SEQ ID NO:3) (20 μM) 1 minute before DAMGO antagonized the effect of DAMGO; DAMGO inhibited the contractions by only 25% after pretreatment with Tyr-Pro-Trp-Phe-OH (SEQ ID NO:3), a 37% attenuation of the opiate agonist effect of DAMGO. Similarly, Tyr-Pro-Phe-Phe-OH (SEQ ID NO:4) at 20 μM and 80 μM provided 12.5% and 35% attenuation, respectively, of the effects of DAMGO. These results indicate that Tyr-Pro-Trp-Phe-OH (SEQ ID NO:3) and Tyr-Pro-Phe-Phe-OH (SEQ ID NO:4) have partial agonist activity.

All of the compositions, methods and apparatus disclosed and claimed herein can be made and executed without undue experimentation in light of the present disclosure. Whereas the compositions and methods of this invention have been described in terms of preferred embodiments, it will be apparent to those of skill in the art that variations may be applied to the compositions, methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Erchegyi, J.; Kastin, A. J.; Zadina, J. E. *Peptides.* 13: 623–631 (1992).
2. Hackler, L.; Kastin, A. J.; Erchegyi, J.; Zadina, J. E. *Neuropeptides.* 24: 159–164 (1993).
3. Erchegyi, J.; Zadina, J. E.; Qiu, X. -D., et al. *Peptide Res.* 6: 31–38 (1993).
4. Zadina, J. E.; Kastin, A. J.; Kenigs, V.; Bruno, C.; Hackler, L. *Neurosci. Lett.* 155: 220–222 (1993).
5. Gergen, K. A.; Zadina, J. E.; Kastin, A. J.; Paul, D. *Eur. J. Pharmacol.* 298: 235–239 (1996).
6. Gergen, K. A.; Zadina, J. E.; Paul, D. *Eur. J Pharmacol.* In Press (1996).
7. Zadina, J. E.; Kastin, A. J.; Ge, L. -J.; Hackler, L. *Life Sci.* 55(24): PL461–466 (1994).
8. Brantl, V.; Gramsch, C.; Lottspeich, F.; Mertz, R.; Jaeger, K. -H.; Herz, A. *Eur. J. Pharmacol.* 125: 309–310 (1986).
9. Erchegyi, J.; Kastin, A. J.; Zadina, J. E.; Qiu, X. -D. *Int. J Peptide Protein Res.* 39: 477–484 (1992).
10. Glamsta, E. -L.; Marklund, A.; Hellman, U.; Wernstedt, C.; Terenius, L.; Nyberg, F. *Regul. Pept.* 34: 169–179 (1991).
11. Brantl, V. *Eur. J. Pharmacol.* 106: 213–214 (1984).
12. Handa, B. K.; Lane, A. C.; Lord, J. A. H.; Morgan, B. A.; Rance, M. J.; Smith, C. F. C. *Eur. J Pharmacol.* 70: 531–540 (1981).
13. Chang, K. -J.; Wei, E. T.; Killian, A.; Chang, J. -K. *J. Pharmacol. Exper. Ther.* 227: 403 (1983).
14. Schiller, P. W.; Nguyen, T. M. -D.; DiMaio, J.; Lemieux, C. *Life Sci.* 33(S1): 319–322 (1983).
15. Bodanszky, M. *Peptide Chemistry: A Practical Textbook,* 2nd edition. Springer-Verlag, New York (1993).
16. Stewart, J. M.; Young, J. D. *Solid Phase Peptide Synthesis,* 2nd edition. Pierce Chemical Company (1984).
17. Schmidt, R.; Neubert, K. *Int. J. Pept. Protein Res.* 37: 502–507 (1991).
18. Prokai-Tatrai, K.; Prokai, L.; Bodor, N. *J. Med. Chem.* 39: 4775–4782 (1996).
19. Wang, J. -X.; Bray, A. M; Dipasquale, A. J.; Maeji, N. J.; Geysen, H. M. *Int. J. Peptide Protein Res.* 42: 384–391 (1993).
20. Corbett, A. D.; Paterson, S. J.; Kosterlitz, H. W. In *Opioids I (Handbook of Exper. Pharmacol.* vol.104/1) Ed. Herz, A., Springer-Verlag, New York. pp. 645–679 (1993).

21. Zadina, J. E.; Kastin, A. J.; Kersh, D.; Wyatt, A. *Life Sci.* 51: 869–885 (1992).
22. Haley, T. J.; McCormick, W. G. Br. *J. Pharmacol. Chemother.* 12: 12–15 (1957).
23. Hylden, J. L. K.; Wilcox, G. L. *J. Pharmacol. Exp. Ther.* 67: 313–316 (1980).
24. Buscher, H. H.; Hill, R. C.; Romer, D., et al. *Nature.* 261: 423–425 (1976).
25. Lenz, G. R.; Evans, S. M.; Walters, D. E.; Hopfinger, A. J. *Opiates.* Academic Press, Orlando, Fla. (1986).
26. Schiller, P. W.; Yam, C. F.; Prosmanne, J. *J. Med. Chem.* 21: 1110–1116 (1978).
27. Cowan, A.; Lewis, J. W. (eds). *Buprenorphine: Combating Drug Abuse with a Unique Opioid.* Wiley-Liss, New York (1995).

What is claimed is:

1. A cyclic peptide having the formula:

H-Tyr-$X_1$-$X_2$-$X_3$ wherein $X_1$ is D-Lys or D-Orn; $X_2$ is Trp, Phe or N-alkyl-Phe wherein the alkyl is 1 to about 6 carbon atoms; $X_3$ is Phe, D-Phe or p-$NO_2$-Phe; and $X_1$ and $X_3$ are covalently connected to form a cyclic peptide.

2. The peptide according to the formula of claim 1 having the formula:

H-Tyr-c-[D-Lys-Trp-Phe].

3. The peptide according to the formula of claim 1 having the formula:

H-Tyr-c-[D-Orn-Trp-Phe].

4. The peptide according to the formula of claim 1 having the formula:

H-Tyr-c-[D-Lys-Phe-Phe].

5. The peptide according to the formula of claim 1 having the formula:

H-Tyr-c-[D-Orn-Phe-Phe].

6. The peptide according to the formula of claim 1 having the formula:

H-Tyr-c-[D-Lys-Trp-p$NO_2$-Phe].

7. The peptide according to the formula of claim 1 having the formula:

H-Tyr-c-[D-Lys-Phe-p$NO_2$-Phe].

8. The peptide according to the formula of claim 1 having the formula:

H-Tyr-c-[D-Orn-Trp-p$NO_2$-Phe].

9. The peptide according to the formula of claim 1 having the formula:

H-Tyr-c-[D-Orn-Phe-p$NO_2$-Phe].

10. The peptide according to the formula of claim 1 having the formula:

H-Tyr-c-[D-Lys-N-Me-Phe-Phe].

11. The peptide according to the formula of claim 1 having the formula:

H-Tyr-c-[D-Orn-N-Me-Phe-Phe].

12. The peptide according to the formula of claim 1 having the formula:

H-Tyr-c-[D-Lys-N-Et-Phe-Phe].

13. The peptide according to the formula of claim 1 having the formula:

H-Tyr-c-[D-Om-N-Et-Phe-Phe].

14. The peptide according to the formula of claim 1 having the formula:

H-Tyr-c-[D-Lys-N-Me-Phe-D-Phe].

15. The peptide according to the formula of claim 1 having the formula:

H-Tyr-c-[D-Lys-N-Et-Phe-D-Phe].

16. A pharmaceutical preparation comprising an effective amount of the peptide, or salts thereof, of claim 1 together with one or more pharmaceutical carriers.

17. A method of activating the mu opiate receptor comprising administering to a patient an effective amount of the peptide of claim 1.

18. A method for providing analgesia to a patient which comprises administering to a patient an effective amount of the peptide of claim 1.

19. A method for providing relief to a patient from gastrointestinal disorders comprising administering to a patient an effective amount of the peptide of claim 1.

20. A method for providing therapy for drug dependence which comprises administering to a patient an effective amount of the peptide of claim 1.

21. A process for screening for $\mu$ receptors comprising:

providing an extract of biological tissue;

contacting said extract with a binding agent composed of a peptide according to claim 14 to form a binding agent—$\mu$ receptor complex; and detecting the complex.

22. The method of claim 19, wherein the gastrointestinal disorder is diarrhea.

23. A method for measuring the quantity of a $\mu$ receptor in a sample, comprising:

selecting a sample suspected of containing a $\mu$ receptor;

contacting the sample and a peptide of claim 1 to form a peptide-$\mu$ receptor complex;

detecting the complex; and quantifying the amount of complex formed.

24. A competitive assay for detecting the presence of a compound that binds to a $\mu$ receptor comprising:

contacting a $\mu$ receptor, a peptide of claim 1, and a sample suspected of containing a compound that binds to a $\mu$ receptor, wherein the peptide and receptor form a peptide-$\mu$ receptor complex;

detecting the concentration of peptide-$\mu$ receptor complex formed; and comparing the concentration of peptide-$\mu$ receptor complex formed with the concentration of peptide-$\mu$ receptor complex formed in the absence of the sample.

25. The process of claim 21, wherein the biological tissue is neuronal tissue.

* * * * *

UNITED STATES PATENT AND TRADEMARK OFFICE
CERTIFICATE OF CORRECTION

PATENT NO. : 5,885,958

DATED : March 23, 1999

INVENTOR(S) : James E. Zadina, Abba J. Kastin, and Laszlo Hackler

It is certified that error appears in the above-identified patent and that said Letters Patent is hereby corrected as shown below:

In column 27, claim 13, line 46, rewrite "D-Om" to read --D-Orn--

In column 28, claim 21, line 23, after "claim", please delete "14" and insert --1--.

Signed and Sealed this

Twentieth Day of July, 1999

Attest:

Q. TODD DICKINSON

*Attesting Officer*          *Acting Commissioner of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified site
        ( B ) LOCATION: 4
        ( D ) OTHER INFORMATION: Phe-NH2 (phenylalanine amide)

( x i ) SEQUENCE DESCRIPTION: SEQ ID NO:1:

Tyr Pro Trp Xaa
1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide     ( i x ) FEATURE:
        ( A ) NAME/KEY: Modified site
        ( B ) LOCATION: 4
            ( c ) OTHER INFORMATION: Phe-NH2 (phenylalanine amide)

( x i ) SEQUENCE DESCRIPTION: SEQ ID NO:2:

Tyr Pro Phe Xaa
1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide     ( x i ) SEQUENCE DESCRIPTION: SEQ ID NO:3:

Tyr Pro Trp Phe
1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) TOPOLOGY: linear (ii) MOLECULE TYPE: peptide (xi) SEQUENCE DESCRIPTION: SEQ ID NO:4:

Tyr Pro Phe Phe
1

(2) INFORMATION FOR SEQ ID NO:5:

(i) SEQUENCE CHARACTERISTICS:
                (A) LENGTH: 4 amino acids
                (B) TYPE: amino acid
                (C) TOPOLOGY: linear (ii) MOLECULE TYPE: peptide (ix) FEATURE:
                (A) NAME/KEY: Modified site
                (B) LOCATION: 4
                        (c) OTHER INFORMATION: D-Phe-NH2 (D-phenylalanine amide)

(xi) SEQUENCE DESCRIPTION: SEQ ID NO:5:

Tyr Pro Trp Xaa
1

(2) INFORMATION FOR SEQ ID NO:6:

(i) SEQUENCE CHARACTERISTICS:
                (A) LENGTH: 4 amino acids
                (B) TYPE: amino acid
                (C) TOPOLOGY: linear (ii) MOLECULE TYPE: peptide (ix) FEATURE:
                (A) NAME/KEY: Modified site
                (B) LOCATION: 4
                        (c) OTHER INFORMATION: D-Phe-NH2 (D-phenylalanine amide)

(xi) SEQUENCE DESCRIPTION: SEQ ID NO:6:

Tyr Pro Phe Xaa
1

(2) INFORMATION FOR SEQ ID NO:7:

(i) SEQUENCE CHARACTERISTICS:
                (A) LENGTH: 4 amino acids
                (B) TYPE: amino acid
                (C) TOPOLOGY: linear (ii) MOLECULE TYPE: peptide (ix) FEATURE:
                (A) NAME/KEY: Modified site
                (B) LOCATION: 4
                        (c) OTHER INFORMATION: pNO2-Phe-NH2
                                (p-nitrophenylalanine amide)

(xi) SEQUENCE DESCRIPTION: SEQ ID NO:7:

Tyr Pro Trp Xaa
1

(2) INFORMATION FOR SEQ ID NO:8:

(i) SEQUENCE CHARACTERISTICS:
                (A) LENGTH: 4 amino acids
                (B) TYPE: amino acid
                (C) TOPOLOGY: linear (ii) MOLECULE TYPE: peptide (ix) FEATURE:

(A) NAME/KEY: Modified site
(B) LOCATION: 4
(c) OTHER INFORMATION: pNO2-Phe-NH2
(p-nitrophenylalanine amide)

(xi) SEQUENCE DESCRIPTION: SEQ ID NO:8:

Tyr Pro Phe Xaa
1

(2) INFORMATION FOR SEQ ID NO:9:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified site
(B) LOCATION: 3
(D) OTHER INFORMATION: N-Me-Phe (N- methyl phenylalanine)

(ix) FEATURE:
(A) NAME/KEY: Modified site
(B) LOCATION: 4
(D) OTHER INFORMATION: Phe-NH2 (phenylalanine amide)

(xi) SEQUENCE DESCRIPTION: SEQ ID NO:9:

Tyr Pro Xaa Xaa
1

(2) INFORMATION FOR SEQ ID NO:10:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified site
(B) LOCATION: 3
(D) OTHER INFORMATION: N-Et-Phe (N- ethyl phenylalanine)

(ix) FEATURE:
(A) NAME/KEY: Modified site
(B) LOCATION: 4
(D) OTHER INFORMATION: Phe-NH2 (phenylalanine amide)

(xi) SEQUENCE DESCRIPTION: SEQ ID NO:10:

Tyr Pro Xaa Xaa
1

(2) INFORMATION FOR SEQ ID NO:11:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified site
(B) LOCATION: 3
(D) OTHER INFORMATION: N-Me-Phe (N- methyl phenylalanine)

(ix) FEATURE:
(A) NAME/KEY: Modified site
(B) LOCATION: 4
(D) OTHER INFORMATION: D-Phe-NH2 (D- phenylalanine amide)

( x i ) SEQUENCE DESCRIPTION: SEQ ID NO:11:

Tyr Pro Xaa Xaa
1

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( D ) TOPOLOGY: linear     ( i i ) MOLECULE TYPE: peptide     ( i x ) FEATURE:
        ( A ) NAME/KEY: Modified site
        ( B ) LOCATION: 3
        ( D ) OTHER INFORMATION: N-Et-Phe (N- ethyl phenylalanine)

( i x ) FEATURE:
        ( A ) NAME/KEY: Modified site
        ( B ) LOCATION: 4
        ( D ) OTHER INFORMATION: D-Phe-NH2 (D- phenylalanine amide)

( x i ) SEQUENCE DESCRIPTION: SEQ ID NO:12:

Tyr Pro Xaa Xaa
1

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide     ( i x ) FEATURE:
        ( A ) NAME/KEY: Modified site
        ( B ) LOCATION: 2
        ( c ) OTHER INFORMATION: D-Lys (D-Lysine)

( x i ) SEQUENCE DESCRIPTION: SEQ ID NO:13:

Tyr Xaa Trp Phe
1

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide     ( i x ) FEATURE:
        ( A ) NAME/KEY: Modified site
        ( B ) LOCATION: 2
        ( c ) OTHER INFORMATION: D-Lys (D-Lysine)

( x i ) SEQUENCE DESCRIPTION: SEQ ID NO:14:

Tyr Xaa Phe Phe
1

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide ( i x ) FEATURE:
  ( A ) NAME/KEY: Modified site
  ( B ) LOCATION: 2
    ( c ) OTHER INFORMATION: D-Orn (D-Ornithine)

( x i ) SEQUENCE DESCRIPTION: SEQ ID NO:15:

Tyr Xaa Trp Phe
1

( 2 ) INFORMATION FOR SEQ ID NO:16:

( i ) SEQUENCE CHARACTERISTICS:
  ( A ) LENGTH: 4 amino acids
  ( B ) TYPE: amino acid
  ( C ) TOPOLOGY: linear  ( i i ) MOLECULE TYPE: peptide  ( i x ) FEATURE:
  ( A ) NAME/KEY: Modified site
  ( B ) LOCATION: 2
    ( c ) OTHER INFORMATION: D-Orn (D-Ornithine)

( x i ) SEQUENCE DESCRIPTION: SEQ ID NO:16:

Tyr Xaa Phe Phe
1

( 2 ) INFORMATION FOR SEQ ID NO:17:

( i ) SEQUENCE CHARACTERISTICS:
  ( A ) LENGTH: 4 amino acids
  ( B ) TYPE: amino acid
  ( C ) TOPOLOGY: linear  ( i i ) MOLECULE TYPE: peptide  ( i x ) FEATURE:
  ( A ) NAME/KEY: Modified site
  ( B ) LOCATION: 2
    ( c ) OTHER INFORMATION: D-Lys (D-Lysine)

( i x ) FEATURE:
  ( A ) NAME/KEY: Modified site
  ( B ) LOCATION: 4
    ( c ) OTHER INFORMATION: pNO2-Phe-NH2
     ( p - n i t r o p h e n y l a l a n i n e   a m i d e )

( x i ) SEQUENCE DESCRIPTION: SEQ ID NO:17:

Tyr Xaa Trp Xaa
1

( 2 ) INFORMATION FOR SEQ ID NO:18:

( i ) SEQUENCE CHARACTERISTICS:
  ( A ) LENGTH: 4 amino acids
  ( B ) TYPE: amino acid
  ( C ) TOPOLOGY: linear  ( i i ) MOLECULE TYPE: peptide  ( i x ) FEATURE:
  ( A ) NAME/KEY: Modified site
  ( B ) LOCATION: 2
    ( c ) OTHER INFORMATION: D-Lys (D-Lysine)

( i x ) FEATURE:
  ( A ) NAME/KEY: Modified site
  ( B ) LOCATION: 4
    ( c ) OTHER INFORMATION: pNO2-Phe-NH2
     ( p - n i t r o p h e n y l a l a n i n e   a m i d e )

( x i ) SEQUENCE DESCRIPTION: SEQ ID NO:18:

Tyr Xaa Phe Xaa (2) INFORMATION FOR SEQ ID NO:19:

(i) SEQUENCE CHARACTERISTICS:
        (A) LENGTH: 4 amino acids
        (B) TYPE: amino acid
        (C) TOPOLOGY: linear     (ii) MOLECULE TYPE: peptide     (ix) FEATURE:
        (A) NAME/KEY: Modified site
        (B) LOCATION: 2
            (c) OTHER INFORMATION: D-Orn (D-Ornithine)

(ix) FEATURE:
        (A) NAME/KEY: Modified site
        (B) LOCATION: 4
            (c) OTHER INFORMATION: pNO2-Phe-NH2
                (p-nitrophenylalanine amide)

(xi) SEQUENCE DESCRIPTION: SEQ ID NO:19:

Tyr Xaa Trp Xaa
1

(2) INFORMATION FOR SEQ ID NO:20:

(i) SEQUENCE CHARACTERISTICS:
        (A) LENGTH: 4 amino acids
        (B) TYPE: amino acid
        (C) TOPOLOGY: linear     (ii) MOLECULE TYPE: peptide     (ix) FEATURE:
        (A) NAME/KEY: Modified site
        (B) LOCATION: 2
            (c) OTHER INFORMATION: D-Orn (D-Ornithine)

(ix) FEATURE:
        (A) NAME/KEY: Modified site
        (B) LOCATION: 4
            (c) OTHER INFORMATION: pNO2-Phe-NH2
                (p-nitrophenylalanine amide)

(xi) SEQUENCE DESCRIPTION: SEQ ID NO:20:

Tyr Xaa Phe Xaa
1

(2) INFORMATION FOR SEQ ID NO:21:

(i) SEQUENCE CHARACTERISTICS:
        (A) LENGTH: 4 amino acids
        (B) TYPE: amino acid
        (C) TOPOLOGY: linear     (ii) MOLECULE TYPE: peptide     (ix) FEATURE:
        (A) NAME/KEY: Modified site
        (B) LOCATION: 2
            (c) OTHER INFORMATION: D-Lys (D-Lysine)

(ix) FEATURE:
        (A) NAME/KEY: Modified site
        (B) LOCATION: 3
            (c) OTHER INFORMATION: N-Me-Phe (N-methyl phenylalanine)

(xi) SEQUENCE DESCRIPTION: SEQ ID NO:21:

Tyr Xaa Xaa Phe
1

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide     ( i x ) FEATURE:
        ( A ) NAME/KEY: Modified site
        ( B ) LOCATION: 2
            ( c ) OTHER INFORMATION: D-Orn (D-Ornithine)

( i x ) FEATURE:
        ( A ) NAME/KEY: Modified site
        ( B ) LOCATION: 3
            ( c ) OTHER INFORMATION: N-Me-Phe (N-methyl phenylalanine)

( x i ) SEQUENCE DESCRIPTION: SEQ ID NO:22:

Tyr Xaa Xaa Phe
1

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide     ( i x ) FEATURE:
        ( A ) NAME/KEY: Modified site
        ( B ) LOCATION: 2
            ( c ) OTHER INFORMATION: D-Lys (D-Lysine)

( i x ) FEATURE:
        ( A ) NAME/KEY: Modified site
        ( B ) LOCATION: 3
            ( c ) OTHER INFORMATION: N-Et-Phe (N-ethyl phenylalanine)

( x i ) SEQUENCE DESCRIPTION: SEQ ID NO:23:

Tyr Xaa Xaa Phe
1

( 2 ) INFORMATION FOR SEQ ID NO:24:

( i ) SEQUENCE CHARACTERISTICS:
        ( A ) LENGTH: 4 amino acids
        ( B ) TYPE: amino acid
        ( C ) TOPOLOGY: linear     ( i i ) MOLECULE TYPE: peptide     ( i x ) FEATURE:
        ( A ) NAME/KEY: Modified site
        ( B ) LOCATION: 2
            ( c ) OTHER INFORMATION: D-Orn (D-Ornithine)

( i x ) FEATURE:
        ( A ) NAME/KEY: Modified site
        ( B ) LOCATION: 3
            ( c ) OTHER INFORMATION: N-Et-Phe (N-ethyl phenylalanine)

( x i ) SEQUENCE DESCRIPTION: SEQ ID NO:24:

Tyr Xaa Xaa Phe
1

( 2 ) INFORMATION FOR SEQ ID NO:25:

( i ) SEQUENCE CHARACTERISTICS:
        ( A ) LENGTH: 4 amino acids
        ( B ) TYPE: amino acid (C) TOPOLOGY: linear (ii) MOLECULE TYPE: peptide (ix) FEATURE:
    (A) NAME/KEY: Modified site
    (B) LOCATION: 2
        (c) OTHER INFORMATION: D-Lys (D-Lysine)

(ix) FEATURE:
    (A) NAME/KEY: Modified site
    (B) LOCATION: 3
        (c) OTHER INFORMATION: N-Me-Phe (N-methyl phenylalanine)

(ix) FEATURE:
    (A) NAME/KEY: Modified site
    (B) LOCATION: 4
        (c) OTHER INFORMATION: D-Phe (D-phenylalanine)

(xi) SEQUENCE DESCRIPTION: SEQ ID NO:25:

Tyr Xaa Xaa Xaa
1

(2) INFORMATION FOR SEQ ID NO:26:

(i) SEQUENCE CHARACTERISTICS:
        (A) LENGTH: 4 amino acids
        (B) TYPE: amino acid
        (C) TOPOLOGY: linear     (ii) MOLECULE TYPE: peptide     (ix) FEATURE:
        (A) NAME/KEY: Modified site
        (B) LOCATION: 2
            (c) OTHER INFORMATION: D-Lys (D-Lysine)

(ix) FEATURE:
        (A) NAME/KEY: Modified site
        (B) LOCATION: 3
            (c) OTHER INFORMATION: N-Et-Phe (N-ethyl phenylalanine)

(ix) FEATURE:
        (A) NAME/KEY: Modified site
        (B) LOCATION: 4
            (c) OTHER INFORMATION: D-Phe (D-phenylalanine)

(xi) SEQUENCE DESCRIPTION: SEQ ID NO:26:

Tyr Xaa Xaa Xaa
1

(2) INFORMATION FOR SEQ ID NO:27:

(i) SEQUENCE CHARACTERISTICS:
        (A) LENGTH: 4 amino acids
        (B) TYPE: amino acid
        (C) TOPOLOGY: linear     (ii) MOLECULE TYPE: peptide     (ix) FEATURE:
        (A) NAME/KEY: Modified site
        (B) LOCATION: 4
            (c) OTHER INFORMATION: Gly-NH2 (glycine amide)

(xi) SEQUENCE DESCRIPTION: SEQ ID NO:27:

Tyr Pro Trp Xaa
1